US008265728B2

(12) United States Patent
MacMahon et al.

(10) Patent No.: US 8,265,728 B2
(45) Date of Patent: Sep. 11, 2012

(54) AUTOMATED METHOD AND SYSTEM FOR THE EVALUATION OF DISEASE AND REGISTRATION ACCURACY IN THE SUBTRACTION OF TEMPORALLY SEQUENTIAL MEDICAL IMAGES

(75) Inventors: Heber MacMahon, Chicago, IL (US); Samuel G. Armato, III, Downers Grove, IL (US)

(73) Assignee: University of Chicago, Chicago, IL (US)

( * ) Notice: Subject to any disclaimer, the term of this patent is extended or adjusted under 35 U.S.C. 154(b) by 1790 days.

(21) Appl. No.: 10/721,827

(22) Filed: Nov. 26, 2003

(65) Prior Publication Data

US 2005/0111718 A1   May 26, 2005

(51) Int. Cl.
*A61B 5/05*    (2006.01)
*A61B 8/00*    (2006.01)

(52) U.S. Cl. ............ 600/407; 600/410; 600/437; 378/5; 378/56; 378/62; 378/98.11; 382/169; 382/171; 382/174; 382/172

(58) Field of Classification Search .................. 600/407, 600/437, 410; 128/653, 660; 378/5, 56, 378/62, 98.11; 382/169–172, 174
See application file for complete search history.

(56) References Cited

U.S. PATENT DOCUMENTS

| | | | |
|---|---|---|---|
| 4,482,918 A | | 11/1984 | Keyes et al. |
| 4,907,156 A | * | 3/1990 | Doi et al. ............... 382/130 |
| 5,570,430 A | * | 10/1996 | Sheehan et al. ............. 382/128 |
| 5,931,780 A | * | 8/1999 | Giger et al. ............... 600/407 |
| 5,987,345 A | | 11/1999 | Engelmann et al. |
| 6,205,348 B1 | * | 3/2001 | Giger et al. ............... 600/407 |
| 6,240,201 B1 | | 5/2001 | Xu et al. |
| 6,282,307 B1 | * | 8/2001 | Armato et al. ............... 382/132 |

(Continued)

FOREIGN PATENT DOCUMENTS

WO          00/25255           5/2000

OTHER PUBLICATIONS

Shoji Kido, et al.; Computerized detection of pulmonary nodules by single-exposure dual-energy computed radiography of the chest (part 1); PII: S0720-048X (02) 00268-1, European Journal of Radiology (EJR) 44 (2002) 198-204.

(Continued)

*Primary Examiner* — Brian Casler
*Assistant Examiner* — Joel Lamprecht
(74) *Attorney, Agent, or Firm* — Oblon, Spivak, McClelland, Maier & Neustadt, L.L.P.

(57) ABSTRACT

An apparatus, method and computer program product for performing computer aided diagnosis on temporal subtraction images of objects. A mode of a gray-level histogram is identified, and a gray-level threshold is established at a predefined fraction of this modal value. All pixels with gray levels below this threshold that lie within the lung regions of the temporal subtraction image remain "on," while all other pixels are set to zero. Area and circularity requirements are imposed to eliminate false-positive regions. Areas of pathologic change identified in this manner may be presented as outlines in the subtraction image or as highlighted regions in the original radiographic image so that, in effect, temporal subtraction becomes a "background" process for computer-aided diagnosis. The present invention is also directed to method, apparatus, and computer program product for performing temporal subtraction on energy subtraction images, with or without subsequent computer aided diagnosis, of objects.

23 Claims, 9 Drawing Sheets

U.S. PATENT DOCUMENTS

| | | | |
|---|---|---|---|
| 6,661,873 B2 * | 12/2003 | Jabri et al. | 378/98.11 |
| 6,690,761 B2 * | 2/2004 | Lang et al. | 378/56 |
| 6,771,736 B2 | 8/2004 | Sabol et al. | |
| 6,782,137 B1 | 8/2004 | Avinash | |
| 6,811,310 B2 * | 11/2004 | Lang et al. | 378/169 |
| 6,956,373 B1 * | 10/2005 | Brown et al. | 324/309 |
| 7,120,225 B2 * | 10/2006 | Lang et al. | 378/54 |
| 7,263,214 B2 * | 8/2007 | Uppaluri et al. | 382/128 |
| 7,282,723 B2 * | 10/2007 | Schomacker et al. | 250/458.1 |
| 7,403,646 B2 * | 7/2008 | Sato | 382/132 |
| 2002/0090126 A1 * | 7/2002 | Oosawa | 382/132 |
| 2002/0102014 A1 | 8/2002 | Ozaki et al. | |
| 2003/0147497 A1 * | 8/2003 | Avinash | 378/98.9 |
| 2003/0152258 A1 * | 8/2003 | Jabri et al. | 382/132 |
| 2003/0215119 A1 * | 11/2003 | Uppaluri et al. | 382/128 |
| 2004/0105527 A1 * | 6/2004 | Ferrant et al. | 378/210 |
| 2004/0225218 A1 * | 11/2004 | Guracar et al. | 600/443 |
| 2004/0252873 A1 * | 12/2004 | Avinash et al. | 382/132 |

OTHER PUBLICATIONS

Shoji Kido, et al., Detection of simulated pulmonary nodules by single-exposure dual-energy computed radiography of the chest: effect of a computer-aided diagnosis system (Part 2); PII: S0720-048 (02) 00269-3; European Journal of Radiology (EJR) 44 (2002) 205-209.

Michael S. Van Lysel, M.S. et al., Work in Progress: Hybrid Temporal-Energy Subtraction in Digital Fluoroscopy; Radiology 147: 869-874, Jun. 1983.

Shigeru Sanada, et al.; Temporal Subtraction Technique for detection of Subtle Anomalies on Temporally Sequential Bone-subtracted Chest Radiographs by Energy Subtraction.; Jpn. J. Radiol. Technol. vol. 56 No. 3.: Mar. 2000.

* cited by examiner

301 — TS image without pathologic change

302 — TS image with pathologic change

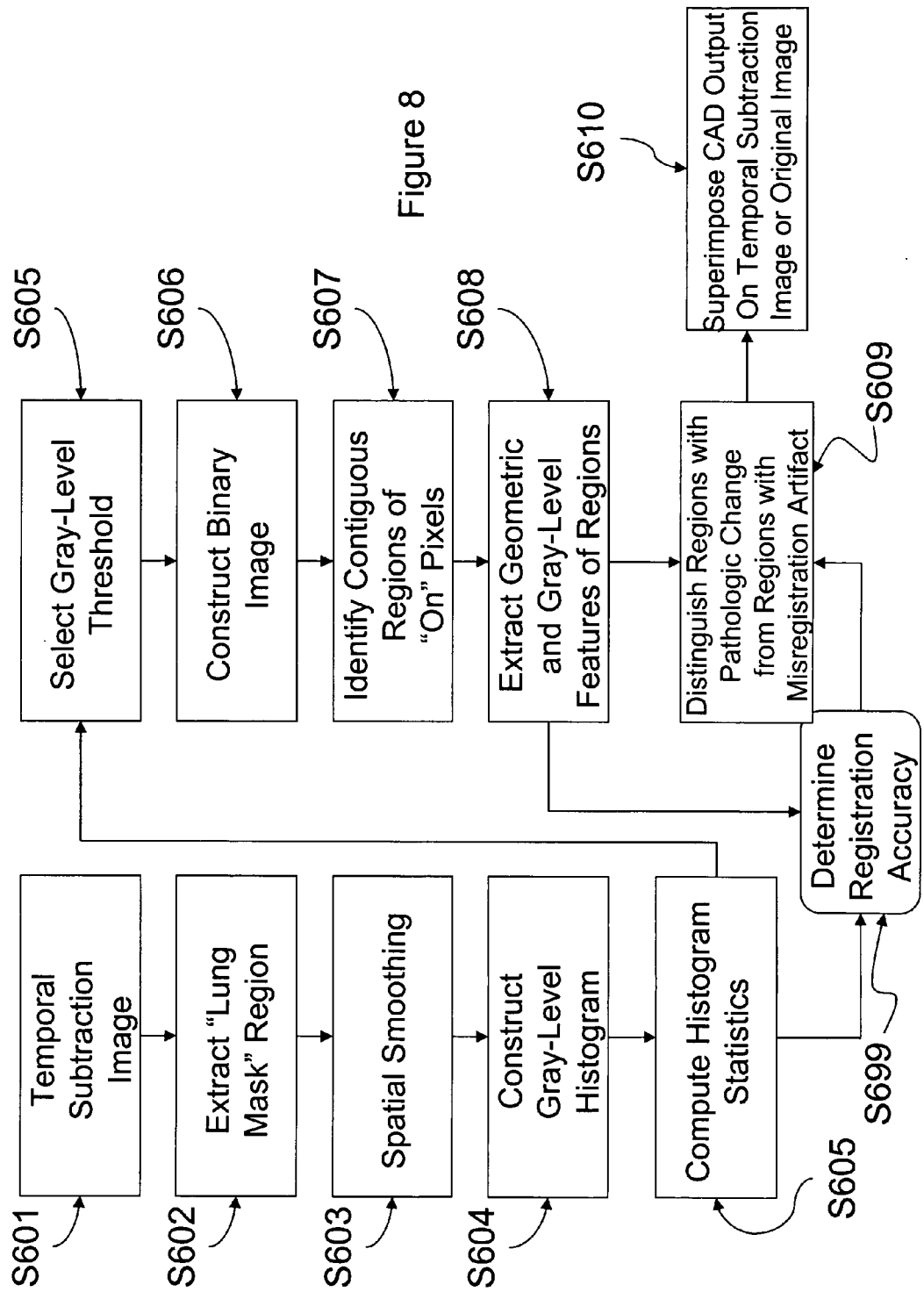

AUTOMATED METHOD AND SYSTEM FOR THE EVALUATION OF DISEASE AND REGISTRATION ACCURACY IN THE SUBTRACTION OF TEMPORALLY SEQUENTIAL MEDICAL IMAGES

The present invention was made in part with U.S. Government support under NIH grant CA64370. The U.S. Government may have certain rights to this invention.

BACKGROUND OF THE INVENTION

Field of the Invention

A method, system, and computer program product for computer aided detection (CAD) of disease with a reduced false positive rate.

The present invention also generally relates to computerized techniques for automated analysis of digital images, for example, as disclosed in one or more of U.S. Pat. Nos. 4,839,807; 4,841,555; 4,851,984; 4,875,165; 4,907,156; 4,918,534; 5,072,384; 5,133,020; 5,150,292; 5,224,177; 5,289,374; 5,319,549; 5,343,390; 5,359,513; 5,452,367; 5,463,548; 5,537,485; 5,598,481; 5,622,171; 5,638,458; 5,657,362; 5,666,434; 5,668,888; 5,740,268; 5,832,103; 5,873,824; 5,881,124; 5,931,780; 5,974,165; 5,982,915; 5,984,870; 5,987,345; 6,011,862; 6,058,322; 6,067,373; 6,075,878; 6,078,680; 6,088,473; 6,112,112; 6,138,045; 6,141,437; 6,185,320; 6,205,348; 6,240,201; 6,282,305; 6,282,307; 6,317,617; 6,335,980; 6,363,163; 6,442,287; 6,470,092 as well as U.S. Pat. Nos. 6,466,689; 6,594,378; Ser. Nos. 09/759,333; 09/760,854; 09/773,636; 09/816,217; 09/830,562; 09/818,831; U.S. Pat. No. 6,438,934; Ser. No. 09/830,574; U.S. Pat. No. 6,577,752; Ser. Nos. 09/990,310; 09/990,311; 09/990,377; 10/078,694; 10/097,820; 10/097,727; 10/120,420; 10/126,523; 10/198,141; 10/231,064; 10/270,674; 10/283,044; 10/292,625; 10/310,836; 10/355,147; 10/357,442; 10/358,337; 10/360,814; 10/366,482; 10/617,675; 60/428,939; 60/429,538; 60/447,295 and 60/514,599; and PCT patent applications PCT/US02/31578; PCT/US02/33651; PCT/US02/33652; PCT/US02/33653; PCT/US02/33654; PCT/US03/02674; PCT/US03/03119; PCT/US03/10468; and PCT/US03/32740, all of which are incorporated herein by reference.

The present invention includes use of various technologies referenced and described in the above-noted U.S. Patents and Applications, as well as described in the references identified in the following List of References. Author(s) and year of publication are cross referenced throughout the specification by reference to the respective number, in parenthesis, of the reference:

LIST OF REFERENCES

1. Kinsey H, Vannelli B D, Fontana R S, et al.: Application of digital image change detection to diagnosis and follow-up of cancer involving the lungs. *Proc SPIE* 70: 99-112, 1975.
2. Kano A, Doi K, MacMahon H, Hassell D D, Giger M L: Digital image subtraction of temporally subtracted chest images for detection of interval change. *Med Phys* 21: 453-461, 1994.
3. Sasaki Y, Katsuragawa S, Ishikawa I, MacMahon H, Doi K: Usefulness of temporally subtracted images in the detection of lung nodules in digital chest radiographs. *Radiology* 201:400, 1996.
4. Difazio M C, MacMahon H, Xu X W, Tsai P, Shiraishi J, Artnato S G Doi K: Digital chest radiography: Effect of temporal subtraction images on detection accuracy. *Radiology* 202: 447-452, 1997.
5. Sasaki Y, Katsuragawa S, MacMahon H, Doi K: Application of temporally subtracted images with mobile computed radiography system in screening chest radiographs. *Proc CAR* pp. 21-24, 1998
6. Katsuragawa S, Sasaki Y, MacMahon H, Ishida T, Doi K: Application of temporal subtraction to screening chest radiographs with a mobile computed radiography system. *Proc 1st International Workshop on Computed-Aided Diagnosis*, pp. 51-56, 1998.
7. Ishida T, Ashizawa K, Engelmann R, Katsuragawa S, MacMahon H, Doi K: Application of temporal subtraction for detection of interval changes in chest radiographs: Improvement of subtraction image using automated initial image matching. *Journal of Digital Imaging* 12: 77-86, 1999.
8. Ishida T, Katsuragawa S, Nakamura K, MacMahon H, Doi K: Iterative image warping technique for temporal subtraction of sequential chest radiographs to detect interval change. *Med Phys* 26: 1320-1329, 1999.
9. Katsuragawa S, Tagashira H, Li Q, MacMahon H, Doi K: Comparison of the quality of temporal subtraction images obtained with manual and automated methods of digital chest radiography. *Journal of Digital Imaging* 12: 166-172, 1999.
10. Nakata H, Nakamura T, Uozumi H, Watanabe T, Aoki, et al.: Clinical usefulness of temporal subtraction on digital chest radiographs. *CARS* 2000 pp. 793-797, 2000.
11. Uozumi T, Nakamura K, Watanabe H, Nakata H, Katsuragawa S, Doi K: ROC analysis of detection of metastatic pulmonary nodules on digital chest radiographs with temporal subtraction. *Academic Radiology* 8: 871-878, 2001.
12. Tsubamoto M, Johkoh T, Kozuka T, Tomiyama N, Hamada S, Honda O, Mihara N, Koyama M, Maeda M, Nakamura H, Fujiwara K: Temporal subtraction for the detection of hazy pulmonary opacities on chest radiography. *AJR* 179: 467-471, 2002.
13. Kakeda S, Nakamura K, Kamada K, Watanabe H, Nakata H, Katsuragawa S, Doi K: Improved detection of lung nodules by using a temporal subtraction technique. *Radiology* 224: 145-151, 2002.
14. Johkoh T, Kozuka T, Tomiyama N, Hamada S, Honda O, Mihara N, Koyama M, Tsubamoto M, Maeda M, Nakamura H, Saki H, Fujiwara K: Temporal subtraction for detection of solitary pulmonary nodules on chest radiographs: evaluation of a commercially available computer-aided diagnosis system. *Radiology* 223: 806-811, 2002.
15. Kido S, Kuriyama K, Kuroda C, Nakamura H, Ito W, Shimura K, Kato H: Detection of simulated pulmonary nodules by single-exposure dual-energy computed radiography of the chest: effect of a computer-aided diagnosis system (Part 2). *European Journal of Radiology* 44(3):205-9, 2002.
16. Kido S, Nakamura H, Ito W, Shimura K, Kato H: Computerized detection of pulmonary nodules by single-exposure dual-energy computed radiography of the chest (part 1). *European Journal of Radiology* 44(3):198-204, 2002.
17. Kido S, Kuriyama K, Hosomi N, Inoue E, Kuroda C, Horai T: Low-cost soft-copy display accuracy in the detection of pulmonary nodules by single-exposure dual-energy subtraction: comparison with hard-copy viewing. *Journal of Digital Imaging* 13(1):33-7, 2000.

18. Kimme-Smith C, Davis D L, McNitt-Gray M, Goldin J, Hart E, Batra P, Johnson T D: Computed radiography dual energy subtraction: performance evaluation when detecting low-contrast lung nodules in an anthropomorphic phantom. *Journal of Digital Imaging* 12(1):29-33, 1999.
19. Kamimura R, Takashima T: Clinical application of single dual-energy subtraction technique with digital storage-phosphor radiography. *Journal of Digital Imaging* 8(1 Suppl 1):21-4, 1995.
20. Kido S, Ikezoe J, Naito H, Arisawa J, Tamura S, Kozuka T, Ito W, Shimura K, Kato H: Clinical evaluation of pulmonary nodules with single-exposure dual-energy subtraction chest radiography with an iterative noise-reduction algorithm. *Radiology* 194(2):407-12, 1995.
21. Kido S, Ikezoe J, Naito H, Tamura S, Kozuka T, Ito W, Shimura K, Kato H: Single-exposure dual-energy chest images with computed radiography. Evaluation with simulated pulmonary nodules. *Investigative Radiology* 28(6): 482-7, 1993.
22. Ito W, Shimura K, Nakajima N, Ishida M, Kato H: Improvement of detection in computed radiography by new single-exposure dual-energy subtraction. *Journal of Digital Imaging* 6(1):42-7, 1993.
23. Katoh T: Theoretical analysis of image formation process in quantitative dual-energy subtraction in a single exposure. *Nippon Igaku Hoshasen Gakkai Zasshi—Nippon Acta Radiologica* 49(9):1152-67, 1989.
24. Ho J T, Kruger R A, Sorenson J A: Comparison of dual and single exposure techniques in dual-energy chest radiography. *Medical Physics* 16(2):202-8, 1989.
25. Ishigaki T, Sakuma S, Ikeda M: One-shot dual-energy subtraction chest imaging with computed radiography: clinical evaluation of film images. *Radiology* 168(1):67-72, 1988.
26. Takashima T: Single exposure energy subtraction chest radiography in the diagnosis of pulmonary cancer. *Nippon Igaku Hoshasen Gakkai Zasshi—Nippon Acta Radiologica* 47(3):455-64, 1987.
27. Ishigaki T, Sakuma S, Horikawa Y, Ikeda M, Yamaguchi, H: One-shot dual-energy subtraction imaging. *Radiology* 161(1):271-3, 1986.
28. Fraser R G, Barnes G T, Hickey N, Luna R, Katzenstein A, Alexander B, McElvein R, Zorn G, Sabbagh E, Robinson C A Jr.: Potential value of digital radiography. Preliminary observations on the use of dual-energy subtraction in the evaluation of pulmonary nodules. *Chest* 89(4 Suppl):249S-252S, 1986.

DISCUSSION OF THE BACKGROUND

Radiologists routinely compare multiple chest radiographs acquired from the same patient over time to facilitate a more complete understanding of changes in anatomy and pathology. Some of these comparisons are merely visual. Some involve comparing CAD results from a first image with CAD results from a later image, e.g., as taught by Roehrig et al. (PCT Publication WO 00/25255), the contents of which are incorporated herein by reference. Some comparisons involve the generation of temporally sequential images which are registered to construct a "temporal subtraction image." This latter technique has proven to be a powerful technique for enhanced visualization of either subtle pathology or small changes in size of more obvious lesions, for example in radiographic chest images (1-14).

Temporal subtraction images are not disease specific. Whereas most applications of computers as a diagnostic aid in radiology have been developed for a specific pathology such as lung nodules or emphysema, temporal subtraction images enhance a radiologist's ability to visualize a wide spectrum of disease. The only requirement is that changes in the size, shape, or density of the disease, as projected in the image plane, exist between the two studies. In conventional systems, once created as a visualization tool, the temporal subtraction image is displayed for radiologist interpretation. A radiologist might have adequate experience interpreting temporal subtraction images, or might feel burdened by the need to review an additional image during a demanding clinical schedule.

What is desired, as discovered by the present inventors, is a computerized approach to temporal subtraction image interpretation that identifies and indicates the locations of regions representing pathologic change. This invention is expected to augment the utility of the temporal subtraction image in clinical practice. Such a computer-aided diagnostic (CAD) method uses computer vision techniques to detect regions of clinical significance.

In addition, temporal subtraction images are constructed from two initial images. The radiologic record of many patients will contain a number of images from which multiple pairwise combinations may be used to construct a sequence of temporal subtraction images. Notable differences may be observed in such a sequence. One pair, for example, may best depict the pathologic change of interest. Moreover, the quality of image registration may not be consistent across all pairs of temporal subtraction images. As a result of poor registration, the clinical utility of certain temporal subtraction images may be limited. Misregistration artifacts in temporal subtraction images typically appear as spatially correlated pairings of dark and bright regions. This relationship is used to evaluate a temporal subtraction image for severity of misregistration and to assist with the differentiation between misregistration and pathologic change. Since the misregistration of images that depict similar anatomy tends to create opposing signals (e.g., bright and dark bands of pixels along a misregistered interface), such misregistration may be identified by the computer and may, if desired, be suppressed to improve the visual quality of any specific temporal subtraction image.

Given that a patient will, in general, have a current radiographic examination and multiple prior examinations, this invention comprises an automated method to select the "best" combination of radiographs for application of a temporal subtraction technique. Ozaki et al. (U.S. Patent Appl. No. 2002/0102014), the contents of which are incorporated herein by reference, teaches a method for automatically producing a predetermined number of temporarily processed images for visual review by a radiologist. However, these conventional methods do not automatically identify a best fit pair based on registration parameters, thus requiring a radiologist to look at all subtraction images rather than the best images. If a patient has more than two temporally sequential radiographic images in their electronic image file, multiple pair-wise combinations of images may be used to construct a sequence of temporal subtraction images. In general, not all such temporal subtraction images will be of equivalent clinical utility. Some combinations might demonstrate pathologic change better than others, and some combinations may demonstrate less desirable registration accuracy. The methods of this invention may be used to identify temporal subtraction images that demonstrate registration accuracy that exceed some predetermined level, while suppressing from radiologists' view those that would contribute very little to the radiologists' decision-making process. In this configuration, the output of the computer-aided diagnosis techniques may or may not be incorporated in the displayed images.

"Best" may indicate the most accurately registered pair of images that results from the temporal subtraction technique, or "best" may indicate the pair of images that, when temporally subtracted, demonstrates the most extensive change in the spatial extent or opacity of disease. The "best" temporal subtraction image or images may be displayed with or without automatically identified CAD derived symbols and information. The automated identification of the "best" temporal subtraction image or images generated from the current image and a sequence of previous images, both in terms of registration accuracy and demonstration of pathologic change, would advance the clinical utility of temporal subtraction images.

Thus, what is desired to perform CAD on temporal subtraction images, as discovered by the present inventors, is a computerized method for the automated detection of change in pulmonary pathology and the automated assessment of image registration accuracy as demonstrated in temporal subtraction images created from radiographic chest image pairs that are taken at different times. In this capacity, what is desired is an ability to automatically determine when a change in the spatial extent or opacity of disease between two radiographs of the same patient is present as indicated in the resulting temporal subtraction image.

Separate from the use of temporal subtraction, in some circumstances energy subtraction techniques may be used to identify medical conditions of interest. Energy subtraction techniques (15-28) exploit the differential attenuation of x-ray photons exhibited by soft-tissue and bony structures at different x-ray energies. Unlike temporal subtraction, which may be performed retrospectively on existing images and requires no alteration to the manner in which the radiographic images are acquired, energy subtraction requires dedicated hardware (now commercially available) to capture a "low-energy image" and a "high-energy image" of the patient during the same radiographic examination. One configuration through which these low- and high-energy images may be acquired requires a single x-ray exposure of the patient; the fluence of x-ray photons transmitted through the patient (i.e., those photons that are not attenuated within the patient) is then recorded with two stacked detectors.

Two principles of physics come into play at this point. First, x-ray tubes generate x-ray beams with a continuous spectrum of energies (the maximum energy of this spectrum is specified by the kVp selected during the examination). Second, lower-energy x-ray photons are preferentially attenuated in matter relative to higher-energy x-ray photons, and the magnitude of this attenuation difference depends on the atomic number of the material (e.g., bone versus soft tissue).

When the x-ray beam transmitted through the patient arrives at the first detector, some fraction of these x-ray photons is absorbed by the detector to record an image, while the remaining photons arrive at the second detector to record a second image. Due to the differential attenuation of x-ray photons in the first detector, the energy spectrum of x-ray photons that arrive at the second detector is shifted toward higher energies relative to the spectrum of x-ray photons that arrive at the first detector. Accordingly, the second detector records information regarding the attenuation of higher energy x-ray photons in the patient, while the first detector records information regarding the attenuation of lower energy x-ray photons in the patient.

Thus, the high energy and low energy images may be captured during a single exposure. The high-energy and low-energy images are then mathematically combined via techniques more complicated than mere subtraction to create a pair of images: a "soft tissue image" (FIG. 6(b)) predominantly depicting structures with attenuation close to that of water and a "bone image" (FIG. 6(c)) predominantly depicting structures with attenuation close to that of calcium. These two images provide a diagnostically powerful combination.

A dual-energy imaging device captures a low-energy image and a high-energy image during a single imaging study, usually during a single exposure of the patient. The "energy-subtraction process" then mathematically manipulates the gray levels of the low- and high-energy images to generate a soft-tissue image, a bone image, and a standard image. Note that only the gray levels are manipulated—the spatial positioning need not be altered since the low- and high-energy images are theoretically spatially aligned to begin with. Of these five images produced, only the soft-tissue, bone, and standard images are provided for further analysis.

Energy subtraction serves a two-fold role in the evaluation of radiographs (e.g., chest radiographs used for lung cancer). First, subtle lung nodules and bone may appear superimposed when projected in two dimensions; the soft-tissue image generated through the energy subtraction process, with bone effectively removed, has the potential to improve radiologists' sensitivity for the detection of such nodules. Second, calcified nodules may be differentiated from non-calcified nodules, since only calcified nodules will appear on the bone image. Accordingly, energy subtraction images may obviate the need for follow-up computed tomography (CT) scans in some situations. Also, as taught in Kido et al. (Eur. Jour. of Radiology 44 (2002) 198-204), these energy subtraction images may then be subjected to computer-aided diagnosis.

The low- and high-energy images acquired during dual-energy imaging also may be combined to construct a standard radiographic image of the chest (FIG. 6(a)) (although typically the low-energy image is used directly as the standard radiographic image) so that a patient with a temporal sequence of n dual-energy imaging studies will have a total of 3n images (a standard radiographic image, a soft tissue image, and a bone image for each study).

Keyes et al. (U.S. Pat. No. 4,482,918), Van Lysel et al. (Radiology, 1983 June; 147(3):889-74), and Sanada et al. (Jpn. J. Radiol. Technol. 2000: 56(3): 428-435), the contents of each of which are incorporated herein by reference, each teach hybrid temporal/energy subtraction where motion artifacts introduced in a common sitting are detected and eliminated. However, the techniques of these references do not compare standard images derived from dual-energy images with historical images derived from dual-energy images to develop registration parameters which are then used to perform temporal subtraction on either bone or soft-tissue images derived from these two temporally disjoint dual-energy images, so as to identify temporal changes in a patient's condition. What is desired, as discovered by the present inventors, is a method, apparatus, and computer program product that combines energy subtraction with temporal subtraction to provide more nuanced views of a patient's condition. This hybrid energy/temporal subtraction image can then be subjected to CAD to automatically identify regions of interest to a radiologist.

SUMMARY OF THE INVENTION

An object of the present invention is a method for detection of pathological changes characterized by good initial detection of pathological regions while simultaneously maintaining a minimum number of false-positives.

Thus, the present invention is directed to a method, system, and computer program product for performing computer aided diagnosis on temporal subtraction images of lung regions. A mode of a gray-level histogram is identified, and a gray-level threshold is established at a predefined fraction of this modal value. All pixels with gray levels below this threshold that lie within the lung regions of the temporal subtraction image remain "on," while all other pixels are set to zero. Area and circularity requirements are imposed on remaining regions to eliminate false-positive regions. Areas of pathologic change identified in this manner may be presented as outlines in the subtraction image or as highlighted regions in the original radiographic image so that, in effect, temporal subtraction becomes a "background" process for computer-aided diagnosis.

The present invention is also directed to method, apparatus, and computer program product for performing temporal subtraction on energy subtraction images, with or without subsequent computer aided diagnosis, of lung regions.

BRIEF DESCRIPTION OF THE DRAWINGS

A more complete appreciation of the present invention and many of the attendant advantages thereof will be readily obtained as the same becomes better understood by reference to the following detailed descriptions and accompanying drawings:

FIG. 1(a) is a chest image of a patient acquired two-and-one-half years prior to the image in FIG. 1(b) and FIG. 1(c) is a temporal subtraction image demonstrating the interval development of primary lung cancers bilaterally, as subsequently confirmed by CT;

FIG. 6(a) is a standard radiographic image, FIG. 6(b) is a soft-tissue image, and FIG. 6(c) is a bone image;

FIG. 7(a) is a dual-energy soft-tissue image that corresponds to the standard radiographic image of FIG. 1(b), while

FIG. 8 is a flow chart of one embodiment of the present invention; and

DETAILED DESCRIPTION OF THE PREFERRED EMBODIMENTS

The automated technique for constructing temporal subtraction images from a specified pair of chest radiographic images has been described in detail previously (see, e.g., references 2, 8, along with U.S. Pat. Nos. 5,359,513, 6,067,373 and 6,594,378 the entire contents of which are incorporated herein by reference). To summarize here, edge-enhancement operations are used to identify the ribcage edge in both the current and previous radiographic images. The current radiographic image (i.e., the image for which temporal comparison is intended to facilitate interpretation) is held fixed as a template for image registration, while the previous image is transformed through rigid body rotation and translation based on a global alignment criterion for the ribcage edges. Local spatial displacement vectors are then computed for regions within the lung fields of the previous radiographic image, which is then "warped" to maximize the cross-correlation of the spatially shifted regions of the previous image and regions within the current image. The two images registered in this manner are then combined such that the gray level of a pixel in the fixed current image is subtracted from the gray level of the corresponding pixel of the warped previous image.

Figures 1A, 1B, 1C:
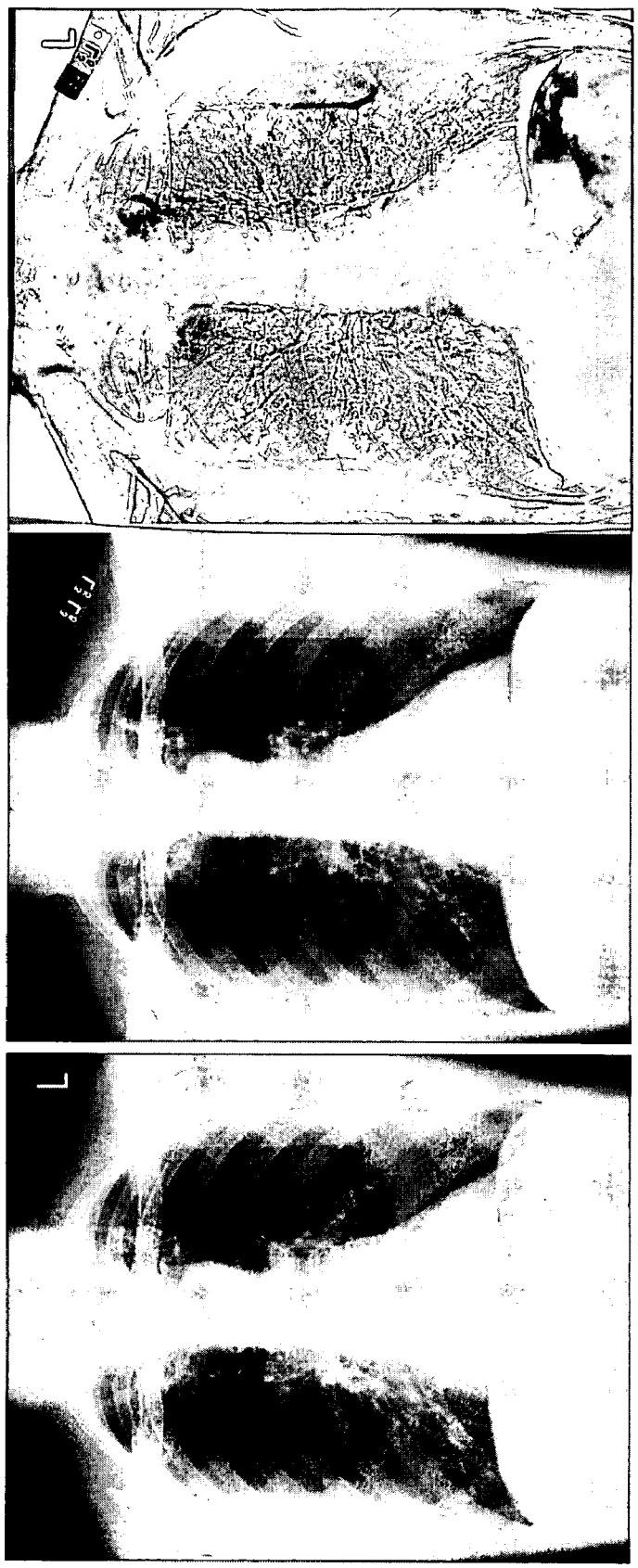
FIGS. 1(a)-1(c) show chest images, where

The result is a "temporal subtraction" image in which dark pixels represent regions that appear more radiographically dense in the current image relative to the corresponding region in the previous image, bright pixels represent regions that appear less radiographically dense in the current image relative to the corresponding region in the previous image, and medium-gray pixels represent regions that exhibit no change between the images. Examples of the conventional approach are shown in FIGS. 1(a)-1(c).

Figure 2:
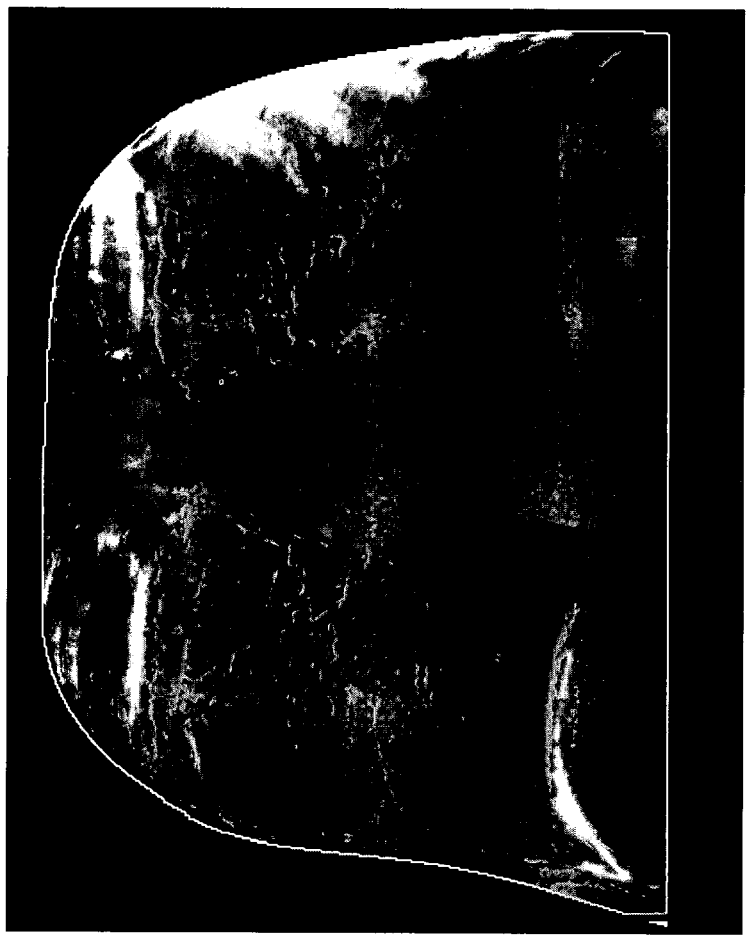
FIG. 2 shows a lung mask region of a temporal subtraction image, where subsequent image analysis is performed within the region of the subtraction image spatially defined by the lung mask.

The "lung mask" provides an important component of the temporal subtraction process. Since subtraction images are intended to enhance the visualization of lung pathology, the temporal subtraction technique seeks to maximize the correlation among pixels within the lungs. Accordingly, a region that encompasses both lungs in the current image (the image to which the previous image will be registered and warped) is automatically identified during construction of the subtraction image. This region, known as the "lung mask," will also encompass both lungs in the temporal subtraction image, since no coordinate transform is performed between the current image and the subtraction image (FIG. 2). In the present invention, subsequent image analysis is performed within the region of the subtraction image spatially defined by the lung mask.

Figure 3B:
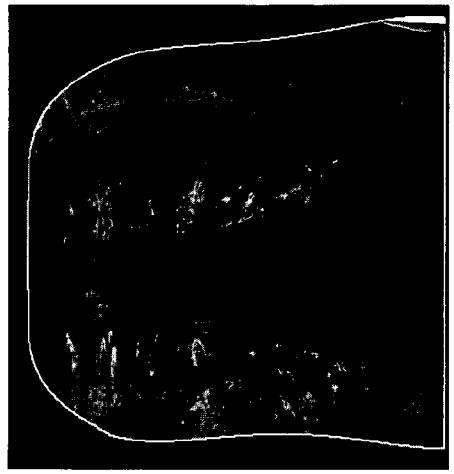
FIG. 3(a) and 3(b) are lung mask regions of temporal subtraction images, where FIG. 3(a) indicates pathological change and FIG. 3(b) indicates no pathological change.
Figure 3A:
Figure 3C:
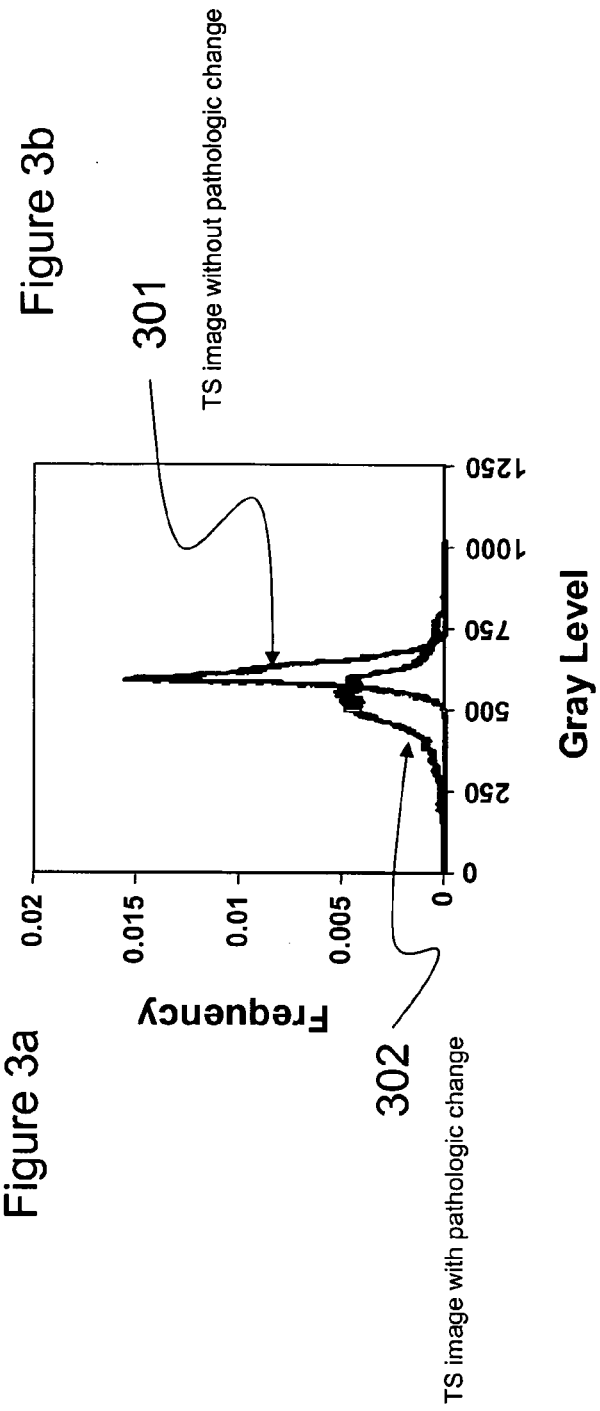
FIG. 3(c) is a graph showing differences in gray-scale for pathological and non-pathological change.

The gray-level histogram constructed from pixels within the lung-mask region of a subtraction image provides important information about the content of the subtraction image. In the limiting case of perfect registration, simulated by the trivial case of subtracting an image from itself, all pixels in the resulting subtraction image would contain the same gray level; a gray-level histogram represented by a delta function would result. In the non-trivial (but ideal) case of optimal image registration between two different images from the same patient with no change in anatomy, pathology, or positioning between the two (for example, two posteroanterior (PA) chest images acquired in succession so that any differences between the two would be due to noise only), the histogram would be represented by a narrow Gaussian curve with a small full-width at half maximum (FWHM). FIGS. 3(a) and 3(b) are lung mask images of a temporal subtraction image demonstrating pathologic change, and a temporal subtraction image without pathologic change, respectively. FIG.

3(c) is chart showing differences between the respective pathologic (302) and non-pathologic (301) gray-level histograms.

In the present invention, for an actual pair of temporally sequential clinical images, the shape and position of the gray-level histogram obtained from the temporal subtraction image are used to identify pathologic change between the two constituent images and to indicate a temporal subtraction image that reflects poor image registration. Histogram shape may be quantified by attributes such as the full-width at half maximum (FWHM), skew, kurtosis, or the standard deviation of a Gaussian function fitted to the histogram. Histogram position may be quantified by attributes such as histogram mean, median, or mode. The CAD techniques that can be applied to the temporal subtraction image are those described in U.S. Pat. Nos. 4,907,156, 5,452,367, 5,598,481, 5,638,458, 5,790,690 and 6,138,045, the entire contents of each which are incorporated herein by reference.

Thus, in the present invention, the lung mask is convolved with a spatial smoothing filter to reduce noise. The gray-level histogram is then constructed from this pre-processed lung mask image. Statistics of this histogram (e.g., mode, mean, skew, and kurtosis) are identified, and a gray-level threshold is established based on these histogram statistics. Since temporal subtraction images represent regions of progressive pathologic change as areas with lower gray levels (i.e., darker) than the average gray level of the image (although the opposite would hold for the progression of certain diseases such as emphysema), all lung mask pixels with gray levels less than this threshold remain "on," while all other pixels are set to zero. Regions of contiguous "on" pixels are identified, and a region-growing technique is applied to spatially dilate the extent of each region.

Figure 4:
FIG. 4 is a temporal subtraction image overlaid with automated pathologic change detection results according to an embodiment of the present invention superimposed (white contour)

In the present invention, morphologic and gray-level features (e.g., area, circularity, mean gray level, and gray-level texture measures) of the dilated regions are computed and used to discriminate between regions corresponding to actual pathologic change and "false-positive" regions that likely represent misregistration artifacts. Areas of pathologic change identified in this manner may be presented as outlines (e.g., 401 in FIG. 4) in the subtraction image or as highlighted regions in the original radiographic image so that, in effect, temporal subtraction becomes a "background" process for computer-aided diagnosis.

Alternatively, a mechanism has been developed by which clinically significant information present in a temporal subtraction image may be intelligently integrated with the original radiographic image. A potential barrier to the widespread clinical use of this powerful technique is the unique appearance of temporal subtraction images, which some radiologists may find unfamiliar or distracting.

Figure 5:
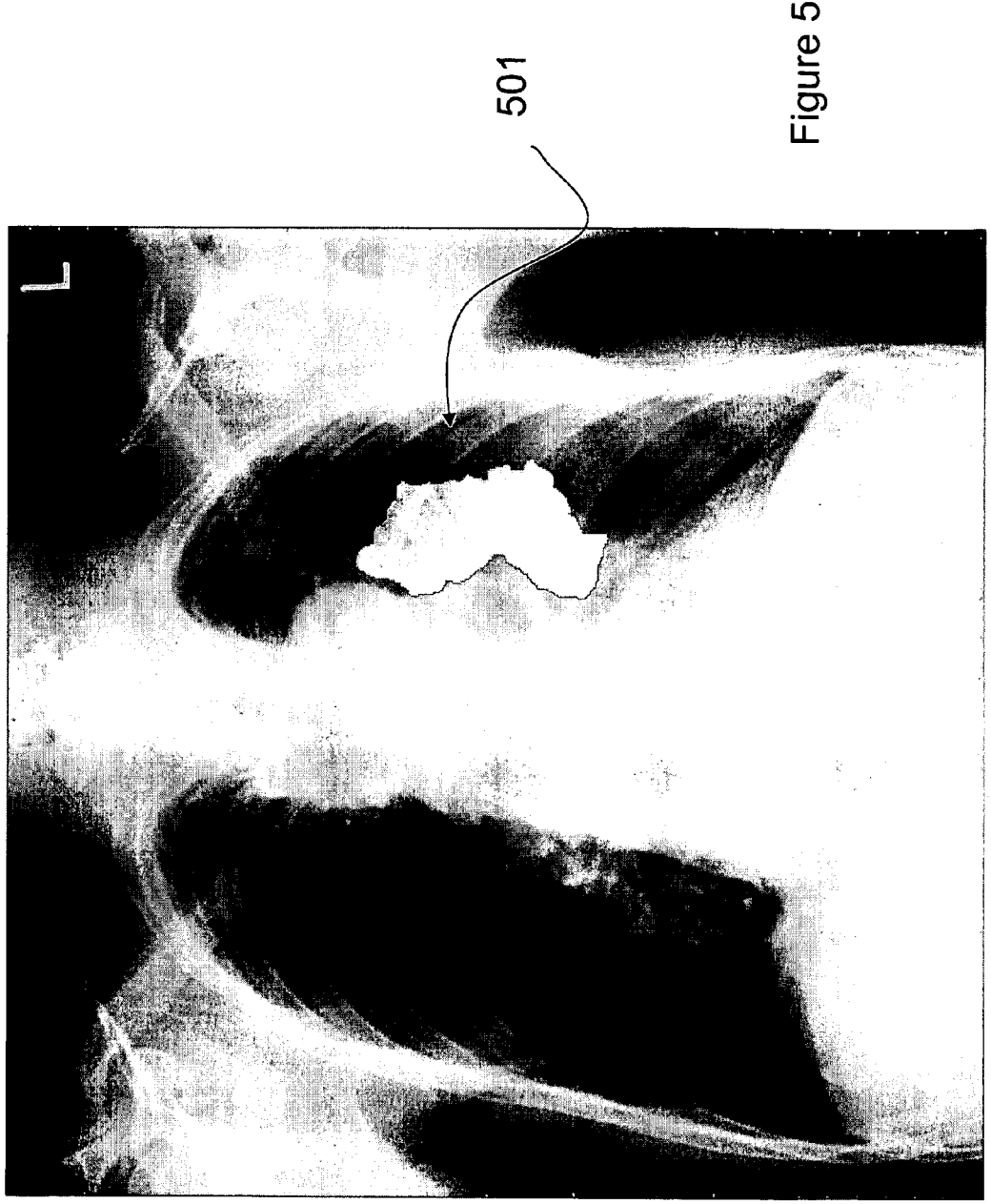
FIG. 5 is a original current image from which the temporal subtraction image in FIG. 4 was derived, where the original current image is overlaid with automated pathologic change detection results according to another embodiment of the present invention superimposed (white image)
Figure 6C:
FIGS. 6(a)-6(c) are images constructed from a conventional dual-energy study, where
Figure 6B:
Figure 6A:
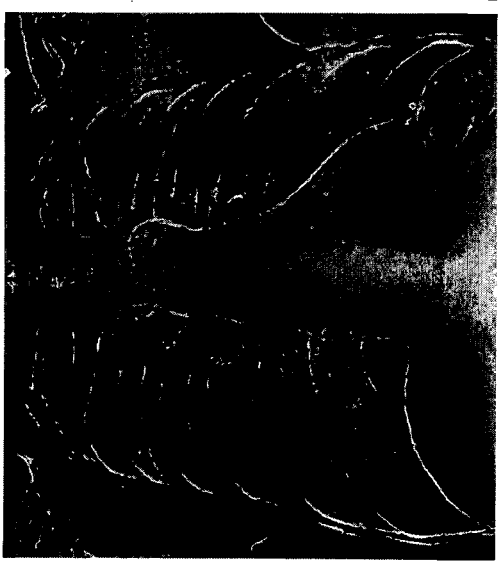
Figure 7B:
FIG. 7(b) is a soft-tissue temporal subtraction image constructed from dual-energy soft-tissue images that correspond to the standard radiographic images of FIGS. 1(a) and 1(b) according to an embodiment of the present invention.
Figure 7A:
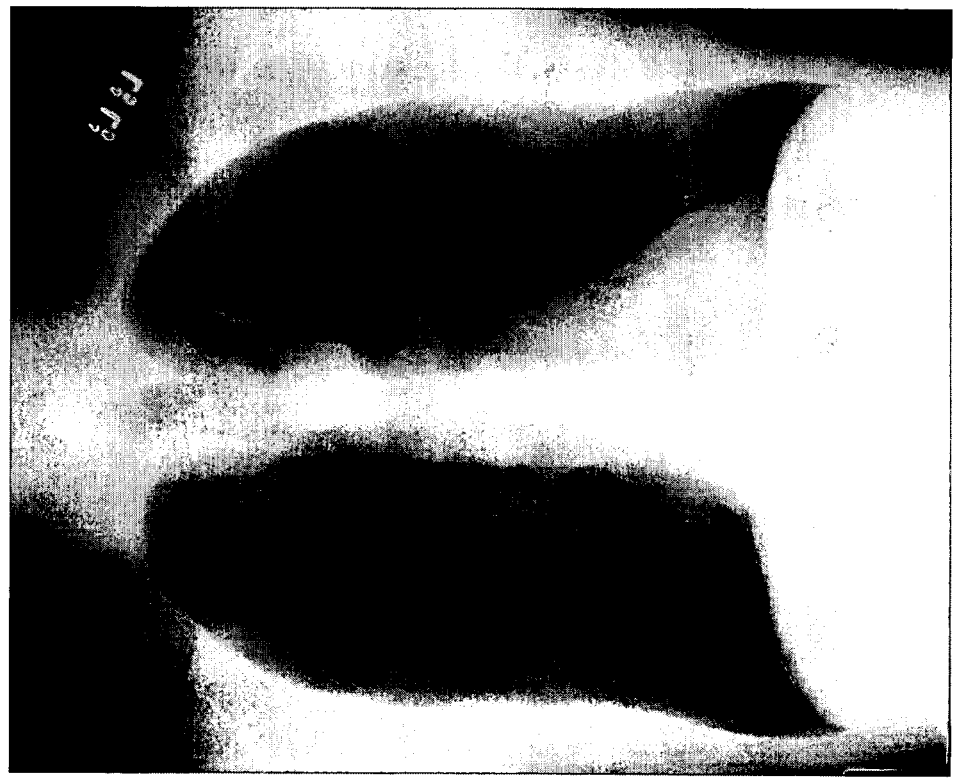

This technique is applicable not only to information derived from temporal subtraction images (including temporal subtraction images obtained from dual-energy studies), but, more broadly, the output of other CAD techniques may be represented in this manner. The method involves superposition of the subtraction image, suitably processed by windowing and global filtering, as a transparent layer on the original image(s). This can result in a more "natural" appearance, while amplifying new abnormalities. An alternative approach requires the identification (presumably through an automated or semi-automated CAD method) of an abnormal region. The CAD output is then displayed within the original radiographic image through an enhancement of the pixels that spatially correspond to the identified abnormal region. Such enhancement involves application of a multiplicative factor, $f(f>1.0)$, to the original gray-level values of these pixels. Alternative methods of enhancing may also be used, including addition of a constant value to the original gray-level values of these pixels. The result can also be overlaid on a current original image (FIG. 5) to provide a more natural radiographic appearance in which abnormalities maintain their internal contrast and relative structural gray-level information but appear, in general, more dense, thus reducing their subtlety. Modifications toward the periphery of the region (501) may be made so that the enhanced region appears to blend with the background in a more continuous manner.

The "false-positive" regions are valuable for the assessment of registration accuracy. Histogram statistics may be used to identify varying degrees of misregistration due to the widening of the gray-level distribution, as previously described. The morphology and spatial distribution of false-positive regions also reflect registration accuracy, since regions of misregistration typically appear as alternating linear bands of dark and bright pixels (caused by rib misregistration, for example). Through a combination of pathologic change detection and registration accuracy assessment, the specific temporal subtraction images that may prove most clinically valuable are identified automatically. If a particular temporal subtraction is of interest despite the presence of misregistration artifacts, visual interpretation of that temporal subtraction image may be enhanced through an automated process that suppresses (through, for example, a median filtering process) the misregistered pixels.

The approach described above considers the entire lung mask region. In another embodiment, the lung mask region may be divided into multiple regions (for example, a quadrant-based approach that separately considers the upper and lower portions of the two lungs). The complete process is then applied independently within each region. This analysis allows for assessment of localized pathologic change and localized registration accuracy.

Thus, the method of the first embodiment is summarized in FIG. 8. The method begins with obtaining a temporal subtraction image (S601). This temporal subtraction image is than subjected to a lung mask to extract a lung mask region (S602). The extracted lung mask region is then subjected to spatial smoothing (S603). The spatially smoothed data is then used to construct a gray level histogram (S604). Histogram statistics are then computed (S605). These histogram statistics are used to determine registration accuracy (S699) as well as to select gray level threshold information (S605). From the gray level threshold information, a binary image is constructed (S606). Within the constructed binary image, contiguous regions of "ON" pixels are identified so as to identify regions of interest (S607). Within these regions of interest, geometric and gray level features are extracted (S608). The extracted geometric and gray level features may also be used to determine registration accuracy (S699). Geometric features include (but are not limited to) mean gray level, gray-level standard deviation, median gray level, and texture measures such as first moment of the power spectrum—all of these may be computed in the temporal subtraction image space as well as in the space of the two constituent original images. Morphologic features include (but are not limited to) eccentricity, compactness, circularity, area, fractal dimension, and orientation of principal axes. The values of these features are input to a rule-based scheme (or an automated classifier such as linear discriminant analysis or an artificial neural network) to distinguish between regions that represent pathologic change and those that represent misregistration. The extracted geometric and gray level features are then compared with the previously derived registration accuracy data so as to distinguish regions with pathological change from regions with misregistration artifacts (S609). The regions with indications of pathologic change are then super imposed as a CAD output onto the temporal subtraction image or on the original image (S610).

As a pilot study, the above-described method was applied to a preliminary database of 12 temporal subtraction images. Six of these images demonstrated no pathologic change between the constituent radiographic images and were considered normal. The other six temporal subtraction images were considered positive for change by an experienced chest radiologist and demonstrated a range of pathology including pleural effusion, interstitial disease, and lung cancer. The method correctly identified six of the eight foci of pathologic change (75%) in the six positive cases and generated no false positives in any of the 12 subtraction images. In one embodiment, features to be extracted include area and circularity where regions smaller than a predefined minimum area or with circularity less than a predefined minimum were excluded as misregistration artifact. In other embodiments, other features may be extracted.

With a fully automated method for the detection of pathologic change in temporal subtraction images of the chest, 75% of regions demonstrating pathologic change in a pilot database of 12 temporal subtraction images were detected correctly with no false positives. Such a computerized method can help radiologists assimilate the results of temporal subtraction in an intuitive way and aid in the identification of disease development and progression.

In an alternative embodiment, the previously described temporal subtraction technique may be applied to images obtained from the energy subtraction process to further the clinical potential of both temporal and energy subtraction. In this alternative embodiment, temporal subtraction may be applied to the standard radiographic images obtained from dual-energy imaging as described previously. That is, the standard radiographic image from the current study is held fixed as a template for image registration, while the standard radiographic image from the previous study is transformed through (1) rigid body rotation and translation based on a global alignment criterion, and (2) local spatial displacements that maximize the cross-correlation of the spatially shifted regions of the previous image and regions within the current image, and the two images registered in this manner are then combined such that the gray level of a pixel in the fixed current image is subtracted from the gray level of the corresponding pixel of the warped previous image.

This process may then be applied to the corresponding soft-tissue images (or to the corresponding bone images) for temporally sequential energy-subtraction studies. Application of the temporal subtraction technique directly to the soft-tissue (or bone images), however, generally may not produce temporal subtraction images with acceptable registration accuracy, since the soft-tissue image and the bone image each contain less anatomic information than the standard radiographic image. Both the rigid body transformations and the local spatial displacements of the temporal subtraction process make use of the anatomic information of two images to achieve proper image registration prior to subtraction.

To overcome this deficit, the temporal subtraction of soft-tissue or bone images may be achieved based on the registration parameters obtained during the temporal subtraction of the standard radiographic image. Since the standard, soft-tissue, and bone images from a particular dual-energy study are intrinsically spatially aligned, registration parameters obtained for the temporal subtraction of the standard radiographic images from two temporally sequential dual-energy studies are applied directly (1) to the soft-tissue images obtained from the same pair of dual-energy studies to obtain a "soft-tissue temporal subtraction image" (FIGS. 5(a)-5(b)) and (2) to the bone images obtained from the same pair of dual-energy studies to obtain a "bone temporal subtraction image."

Because the warping process requires anatomic details to identify the most appropriate shift vectors, it is preferred to obtain the shift vectors from the image that contains the most anatomic detail, which is the standard image. However, in other embodiments shift vectors can also be obtained from the other images. Once the shift vectors are obtained based on the standard images obtained from temporally spaced dual-energy imaging studies, these shift vectors are applied to the soft-tissue images to produce a 'warped' soft-tissue image. Then the "warped" soft-tissue image will be subtracted from the other soft-tissue image to obtain a soft-tissue temporal subtraction image (again, "bone" may replace every occurrence of "soft-tissue" to describe the construction of a bone temporal subtraction image).

Once a soft-tissue temporal subtraction image and a bone temporal subtraction image are constructed in this manner, the automated techniques for the identification of pathologic change in temporal subtraction images may be applied. Again, examples of these automated techniques include those described in U.S. Pat. No. 5,987,345. Then, the concepts described previously (spatial smoothing, distribution of the gray-level histogram, gray-level thresholding, and features of the surviving regions) are used to identify pathologic change in the soft-tissue temporal subtraction and the bone temporal subtraction images.

Figure 9:
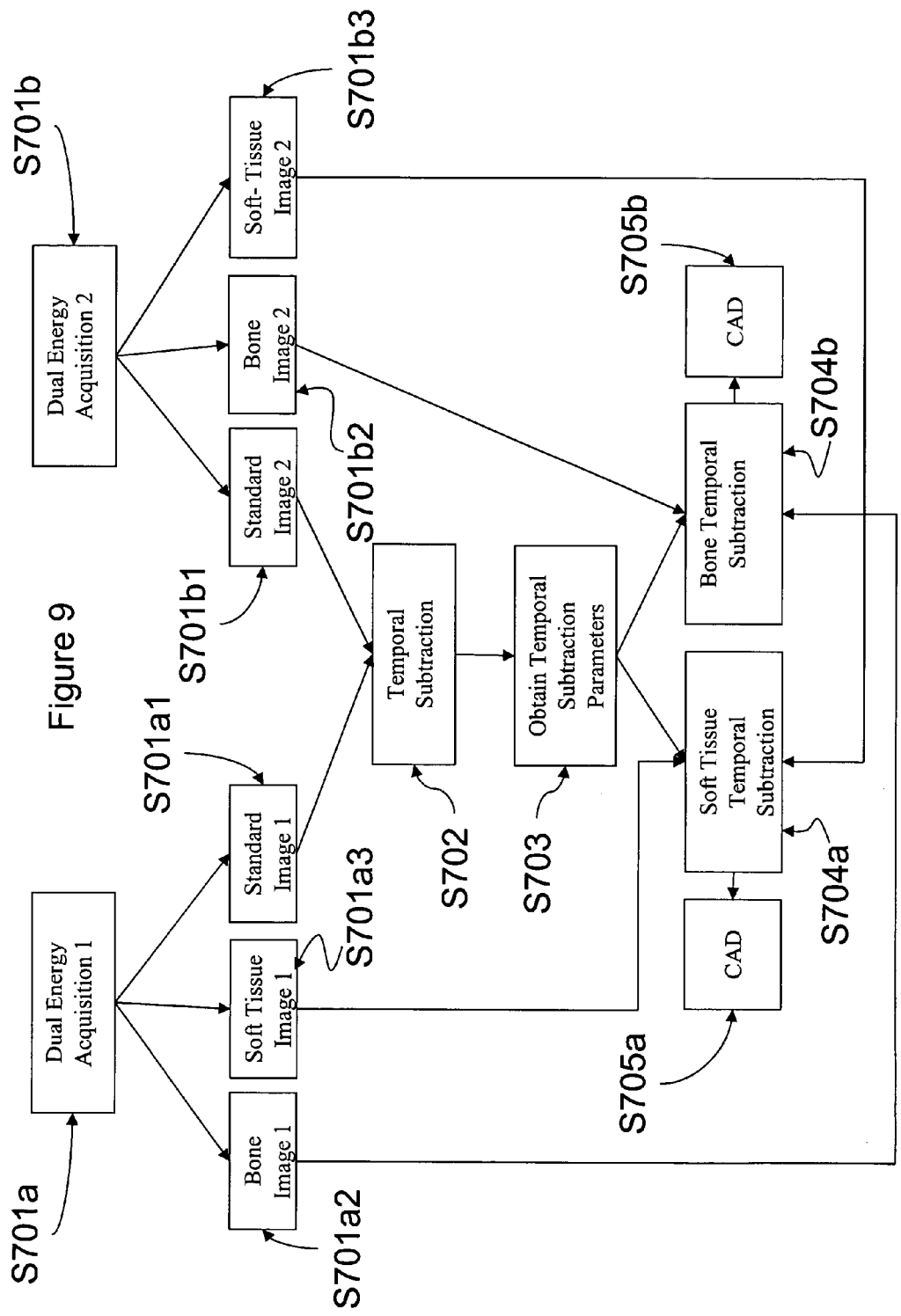
FIG. 9 is a flow chart of another embodiment of the present invention.

The method of the second embodiment is summarized in FIG. 9. Dual energy images are obtained at separate times (S701A, S701B). Each dual energy acquisition results in a standard image (S701A1, S701B1), a soft tissue image (S701A3, S701B3), and a bone image (S701A2, S701B2). The standard images obtained from the two dual energy acquisition steps are then subjected to temporal subtraction (S702), from which temporal subtraction parameters are obtained (S703). These temporal subtraction parameters are then used in a corresponding soft tissue temporal subtraction (S704A) and/or a bone temporal subtraction (S704B) process. The soft tissue temporal subtraction (S704A) is exercised against the soft tissue images obtained from the two dual energy acquisitions (S701A3, S701B3). Similarly, the bone temporal subtraction process (S704B) is exercised against the bone images obtained from the two dual energy acquisitions (S701A2, S701B2). The soft tissue temporal subtraction data and/or bone temporal subtraction data are then subjected to corresponding computer-aided diagnosis (S705A, S705B) according to the method shown in FIG. 8.

The present invention conveniently may be implemented using a conventional general purpose computer or microprocessor programmed according to the teachings of the present invention, as will be apparent to those skilled in the computer art. Appropriate software may readily be prepared by programmers of ordinary skill based on the teachings of the present disclosure, as will be apparent to those skilled in the software art.

As disclosed in cross-referenced U.S. patent application Ser. No. 09/773,636, a computer 900 may implement the methods of the present invention, wherein the computer housing houses a motherboard which contains a CPU, memory (e.g., DRAM, ROM, EPROM, EEPROM, SRAM, SDRAM, and Flash RAM), and other optional special purpose logic devices (e.g., ASICS) or configurable logic devices (e.g., GAL and reprogrammable FPGA). The computer also includes plural input devices, (e.g., keyboard and mouse), and a display card for controlling a monitor. Additionally, the computer may include a floppy disk drive; other removable media devices (e.g. compact disc, tape, and removable magneto-optical media); and a hard disk or other fixed high density media drives, connected using an appropriate device bus (e.g., a SCSI bus, an Enhanced IDE bus, or an Ultra DMA bus). The computer may also include a compact disc reader, a compact disc reader/writer unit, or a compact disc jukebox, which may be connected to the same device bus or to another device bus.

Examples of computer readable media associated with the present invention include compact discs, hard disks, floppy disks, tape, magneto-optical disks, PROMs (e.g., EPROM, EEPROM, Flash EPROM), DRAM, SRAM, SDRAM, etc. Stored on any one or on a combination of these computer readable media, the present invention includes software for controlling both the hardware of the computer and for enabling the computer to interact with a human user. Such software may include, but is not limited to, device drivers, operating systems and user applications, such as development tools. Computer program products of the present invention include any computer readable medium which stores computer program instructions (e.g., computer code devices) which when executed by a computer causes the computer to perform the method of the present invention. The computer code devices of the present invention may be any interpretable or executable code mechanism, including but not limited to, scripts, interpreters, dynamic link libraries, Java classes, and complete executable programs. Moreover, parts of the processing of the present invention may be distributed (e.g., between (1) multiple CPUs or (2) at least one CPU and at least one configurable logic device) for better performance, reliability, and/or cost. For example, an outline or image may be selected on a first computer and sent to a second computer for remote diagnosis.

The present invention may also be complemented with addition filtering techniques and tools to account for nodule contrast, degree of irregularity, texture features, etc.

The invention may also be implemented by the preparation of application specific integrated circuits or by interconnecting an appropriate network of conventional component circuits, as will be readily apparent to those skilled in the art.

The source of image data to the present invention may be any appropriate image acquisition device such as an X-ray machine, ultrasound machine, CT apparatus, and MRI apparatus. Further, the acquired data may be digitized if not already in digital form. Alternatively, the source of image data being obtained and processed may be a memory storing data produced by an image acquisition device, and the memory may be local or remote, in which case a data communication network, such as PACS (Picture Archiving Computer System), may be used to access the image data for processing according to the present invention.

Numerous modifications and variations of the present invention are possible in light of the above teachings. It is therefore to be understood that within the scope of the appended claims, the invention may be practiced otherwise than as specifically described herein. For example, the previously described methods, devices, and computer program products may be adapted for use against organs other than lungs (e.g., liver, heart, brain, breast, etc.). Similarly, the pathologic changes to be identified may be cancerous or non-cancerous. Also, the previously described methods, devices, and computer program products may be adapted for use with X-ray, CT, sonography, MRI, and other non-invasive examination technologies.

The invention claimed is:

1. A method, comprising:
    obtaining a temporal subtraction image of an anatomical region of a patient by registering two images taken at respective times separated by a time interval that is long enough to allow for pathological change in the anatomical region;
    extracting at least one feature from the registered subtraction image;
    classifying a region of interest in the registered subtraction image as one of (1) a misregistration or motion artifact, and (2) an abnormality associated with said pathological change, based on the extracted at least one feature by inputting the at least one feature into an automated classifier performed on a processor; and
    displaying at least one of a temporal subtraction image and the two images and computer-aided diagnostic symbol indicating a location of a region representing said pathological change on the at least one of the temporal subtraction image and the two images.

2. The method of claim 1, wherein the extracting step comprises:
    constructing a gray-level histogram from the temporal subtraction image;
    constructing a binary image based on the gray-level histogram; and
    extracting at least one feature from the gray-level histogram.

3. The method of claim 2, wherein the classifying step comprises:
    determining a registration accuracy based on the gray-level histogram.

4. The method of claim 1, wherein said extracting step comprises:
    identifying an organ mask region; and
    spatially smoothing said organ mask region.

5. The method of claim 1, wherein said extracting step comprises:
    producing a histogram of pixels in the subtraction image;
    determining a threshold level based on the produced histogram;
    thresholding the subtraction image using said threshold and identifying ON and OFF pixels based on the thresholding;
    identifying a contiguous region of ON pixels; and
    extracting at least one of geometric or gray-level feature from said contiguous region.

6. The method of claim 1, wherein said displaying step comprises:
    obtaining a first dual-energy image, a first standard image, and one of a first bone image and a first soft tissue image from the first dual-energy image at a first point in time;
    obtaining a second dual-energy image, a second standard image, and one of a second bone image and a second soft tissue image from the second dual-energy image at a second point in time;
    using the first and second standard images to obtain shift vectors to obtain image registration;
    performing temporal subtraction, using said shift vectors, on one of the first and second bone images or one of the first and second soft tissue images to produce a temporally subtracted image; and
    outputting the temporally subtracted image.

7. The method of claim 6, wherein said displaying step comprises:
    outputting the temporally subtracted image to a display and displaying the temporally subtracted image.

8. The method of claim 6, wherein said displaying step comprises:
outputting the temporally subtracted image to a processor; and
performing computer aided diagnosis on the subtracted image.

9. The method of claim 8, wherein said step of performing computer aided diagnosis comprises:
identifying pathological change in the temporally subtracted image.

10. The method of claim 9, wherein said identifying step comprises:
constructing a gray-level histogram from the temporally subtracted image;
constructing a binary image based on the gray-level histogram; and
determining a registration accuracy of the gray-level histogram.

11. The method of claim 8, further comprising:
superimposing a computer-aided diagnostic symbol on at least a selected one of the temporal subtraction image, the first dual-energy image, the first standard image, the first bone image, the first soft tissue image, the second dual-energy image, the second standard image, the second bone image, and the second soft tissue image; and
displaying the selected one of the temporal subtraction image, the first dual-energy image, the first standard image, the first bone image, the first soft tissue image, the second dual-energy image, the second standard image, the second bone image, and the second soft tissue image with the computer-aided diagnostic symbol superimposed thereon.

12. A non-transitory computer-readable medium storing instructions that, when executed, cause a computing device to perform the steps of claim 1.

13. An apparatus, comprising:
a subtraction unit configured to obtain a temporal subtraction image of an anatomical region of a patient by registering two images taken at respective times separated by a time interval that is long enough to allow for pathological change in the anatomical region;
an extraction unit configured to extract at least one feature from the registered subtraction image;
means for classifying a region of interest in the registered subtraction image as one of (1) a misregistration or motion artifact, and (2) an abnormality associated with said pathological change, based on the extracted at least one feature, by inputting the at least one feature into an automated classifier; and
a display unit configured to superimpose a computer-aided diagnostic symbol indicating a location of a region representing said pathological change on at least one of the temporal subtraction image and the two images.

14. The apparatus of claim 13, wherein the extraction unit comprises:
means for constructing a gray-level histogram from the temporal subtraction image;
means for constructing a binary image based on the gray-level histogram; and
means for extracting at least one feature from the gray-level histogram.

15. The apparatus of claim 14, wherein the means for classifying comprises:
means for determining a registration accuracy based on the gray-level histogram.

16. The apparatus of claim 13, wherein said extraction unit comprises:
means for identifying an organ mask region; and
means for spatially smoothing said organ mask region.

17. The apparatus of claim 13, wherein said extraction unit comprises:
means for producing a histogram of pixels in the subtraction image;
means for determining a threshold level based on the produced histogram;
means for thresholding the subtraction image using said threshold and identifying ON and OFF pixels based on the threshold;
means for identifying a contiguous region of ON pixels; and
means for extracting at least one of geometric or gray-level feature from said contiguous region.

18. The apparatus of claim 13, wherein said subtraction unit comprises:
means for obtaining a first dual-energy image, a first standard image, and one of a first bone image and a first soft tissue image from the first dual-energy image at a first point in time;
means for obtaining a second dual-energy image, a second standard image, and one of a second bone image and a second soft tissue image from the second dual-energy image at a second point in time;
means for using the first and second standard images to obtain shift vectors to obtain image registration;
means for performing temporal subtraction, using said shift vectors, on one of the first and second bone images or one of the first and second soft tissue images to produce a temporally subtracted image; and
means for outputting the temporally subtracted image.

19. The apparatus of claim 18, wherein said display unit comprises:
means for outputting the temporally subtracted image to a display and displaying the temporally subtracted image.

20. The apparatus of claim 18, wherein said display unit comprises:
means for outputting the temporally subtracted image to a processor; and
means for performing computer aided diagnosis on the subtracted image.

21. The apparatus of claim 20, wherein said means for performing computer aided diagnosis comprises:
means for identifying pathological change in the temporally subtracted image.

22. The apparatus of claim 21, wherein said means for identifying comprises:
means for constructing a gray-level histogram from the temporally subtracted image;
means for constructing a binary image based on the gray-level histogram; and
means for determining a registration accuracy of the gray-level histogram.

23. The apparatus of claim 20, further comprising:
means for superimposing a computer-aided diagnostic symbol on at least a selected one of the temporal subtraction image, the first dual-energy image, the first standard image, the first bone image, the first soft tissue image, the second dual-energy image, the second standard image, the second bone image, and the second soft tissue image; and
means for displaying the selected one of the temporal subtraction image, the first dual-energy image, the first standard image, the first bone image, the first soft tissue image, the second dual-energy image, the second standard image, the second bone image, and the second soft tissue image with the computer-aided diagnostic symbol superimposed thereon.

* * * * *